United States Patent
Underhill et al.

(10) Patent No.: US 6,576,810 B1
(45) Date of Patent: Jun. 10, 2003

(54) TOILET TRAINING ARTICLE CONTAINING AN EFFERVESCENT AGENT

(75) Inventors: Richard L. Underhill, Neenah, WI (US); Marsha M. Malone, Appleton, WI (US); Bernard J. Minerath, III, Oshkosh, WI (US); Beth A. Lange, Appleton, WI (US); Duane G. Krzysik, Appleton, WI (US); David W. Koenig, Menasha, WI (US); Kimberly M. Bleck, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 217 days.

(21) Appl. No.: 09/696,747

(22) Filed: Oct. 25, 2000

(51) Int. Cl.⁷ .......................... A61F 13/15; A61L 15/00
(52) U.S. Cl. ...................... 604/361; 604/358; 604/364; 424/43; 424/44
(58) Field of Search ................ 424/43, 44; 604/358, 604/361, 362, 364; 428/905

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,289,794 A | 9/1981 | Kleiner et al. |
| 4,340,563 A | 7/1982 | Appel et al. |
| 4,790,836 A | 12/1988 | Brecher |
| 4,940,464 A | 7/1990 | Van Gompel et al. |
| 5,342,535 A | 8/1994 | Ramirez et al. |
| 5,649,914 A | 7/1997 | Glaug et al. |
| 5,658,268 A | 8/1997 | Johns et al. |
| 5,681,298 A | 10/1997 | Brunner et al. |
| 5,702,376 A | 12/1997 | Glaug et al. |
| 5,702,377 A | 12/1997 | Collier, IV et al. |
| 5,733,272 A | 3/1998 | Brunner et al. |
| 5,766,389 A | 6/1998 | Brandon et al. |
| 5,797,892 A | 8/1998 | Glaug et al. |
| 5,885,264 A | 3/1999 | Matsushita |
| 5,891,124 A | 4/1999 | Nomura et al. |
| 6,369,290 B1 * | 4/2002 | Glaug et al. ................ 424/490 |
| 6,451,331 B1 * | 9/2002 | Slavtcheff et al. .......... 424/401 |

FOREIGN PATENT DOCUMENTS

| | | |
|---|---|---|
| JP | 11-178854 | 7/1999 |
| WO | WO94/24994 A1 | 11/1994 |
| WO | WO 00/37009 | 6/2000 |
| WO | WO01/56542 A1 | 8/2001 |
| WO | WO01/60299 A1 | 8/2001 |

OTHER PUBLICATIONS

International Search Report for PCT/US01/29557.

* cited by examiner

*Primary Examiner*—Terrel Morris
*Assistant Examiner*—Jennifer Boyd
(74) *Attorney, Agent, or Firm*—Senniger, Powers, Leavitt & Roedel

(57) ABSTRACT

A toilet training article in the form of a toilet training pad containing an effervescent agent is disclosed. The toilet training pad, which may be an insertable pad or integrated directly into an undergarment, contains an effervescent agent which releases gas upon being contacted by urine. The effervescent agent may be in the form of a compound containing a substantially inert gas, or may be a combination of compounds that, upon being contacted by urine, produce a gas.

37 Claims, 2 Drawing Sheets

TOILET TRAINING ARTICLE CONTAINING AN EFFERVESCENT AGENT

BACKGROUND OF THE INVENTION

The present invention relates to an article for assisting humans, particularly children, in toilet training. More specifically, the present invention relates to an article in the form of a pliable pad containing an effervescent agent or material which when worn facilitates the toilet training process by providing a release of gas next to the skin of the wearer during and/or after urination occurs to alert or signal the wearer.

Disposable absorbent training pants are useful in toilet training children. Typically, these undergarments are similar to washable, cloth underwear in how they are put on and worn, yet also provide an absorbent function like diapers to draw and retain urine away from the skin of the wearer. Training pants provide a child undergoing toilet training with an undergarment which eases the transition from diapers to washable, cloth underwear as they become more confident in their ability to use the toilet independently.

In order to learn to use the toilet independently, a child must first recognize when urination has occurred so that this bodily function may be controlled. This recognition can represent a substantial hurdle in the training process as urination may often occur during an activity that distracts the child sufficiently so that the child does not notice urination. Also, a child's ability to recognize when urination occurs may be hampered by the improved performance of disposable absorbent undergarments which quickly draw and retain urine away from the wearer's skin after an insult occurs.

Many believe that a child must feel the sensation of wetness on the skin after urination in order to facilitate awareness of this bodily function and promote timely use of the toilet so as to avoid the uncomfortable feeling which otherwise follows. Although this belief is embraced by many, such practice may expose a child to increased risk of skin irritations and rashes caused by prolonged and repeated contact with urine.

Several attempts have been made at providing toilet training aids which alert a child that urination has occurred. For example, pads adapted for releasable attachment to the crotch and/or buttocks region of a disposable toilet training pant, diaper or other undergarment and including a temperature change member and/or a dimensional change member which provide a temperature change or dimensional change sensation when contacted with urine to alert the child wearing the undergarment that urination has occurred have been fabricated. Also absorbent articles are disclosed that when first insulted, have a high initial surface moisture value or wet feel to alert the child that urination has occurred. This initial wetness lasts only a short time after which the surface moisture value drops to a lower level resulting in a drier feeling to the child and increased comfort.

Although there has been substantial progress in toilet training aids, there continues to be a need for simple, effective articles that alert children that urination has occurred.

SUMMARY OF THE INVENTION

The present invention concerns a toilet training article which alerts the wearer that urination has occurred. The toilet training article is in the form of a pad worn in conjunction with an undergarment. The pad may be made an integral part of the undergarment, or may be adapted for releasable or permanent attachment to the undergarment by a purchaser. The pad contains an effervescent agent or combination of agents that alerts the wearer that urination has occurred by releasing gas and causing a mild concussive (i.e., "popping," "crackling," "bubbling" or "fizzing") sensation on or next to the wearer's skin upon urination. This may be accomplished, if desired, without trapping moisture against the skin of the wearer. The present invention can be used in a variety of absorbent undergarments.

Briefly, therefore, the present invention is directed to an article in the form of a pad comprising a pliable substrate containing an effervescent agent. The substrate has a body side face and an outside face, and the body side face faces the skin of the wearer when the article is worn. The effervescent agent is disposed on the substrate in a manner such that when the pad is wetted with urine, the effervescent agent releases a gas to alert the wearer of urination.

The invention is further directed to a process for manufacturing an article in the form of a pad comprising a pliable substrate and an effervescent agent. The process comprises first mixing the effervescent agent with an adhesive and then applying the mixture onto the substrate and allowing the mixture to dry.

The invention is further directed to a process for manufacturing an article in the form of a pad comprising a pliable substrate including a gas-permeable fibrous matrix and an effervescent agent. The process comprises depositing the effervescent agent onto the gas-permeable fibrous matrix and passing a gas through the gas-permeable fibrous matrix to force the effervescent agent to become entrapped in the fibrous matrix.

The invention is further directed to a toilet training article. The article comprises a three-dimensional toilet training undergarment having an inner surface, a pad comprising a pliable substrate, an effervescent agent disposed on the substrate, and an attachment means for releasably attaching the pad to the inner surface of the toilet training undergarment.

The invention is further directed to a method for making a wearer aware of having voided urine. The method comprises placing an article next to the skin of the wearer, the article being in the form of a pad comprising a pliable substrate and an effervescent agent. The effervescent agent is disposed in contact with the substrate in a manner such that when the pad is wetted with urine voided by the wearer, the effervescent agent produces a gas.

Other embodiments and features of this invention will be in part apparent and in part pointed out hereinafter.

BRIEF DESCRIPTION OF THE DRAWINGS

Corresponding reference characters indicate corresponding parts throughout the drawings.

DEFINITIONS

Figure 1:
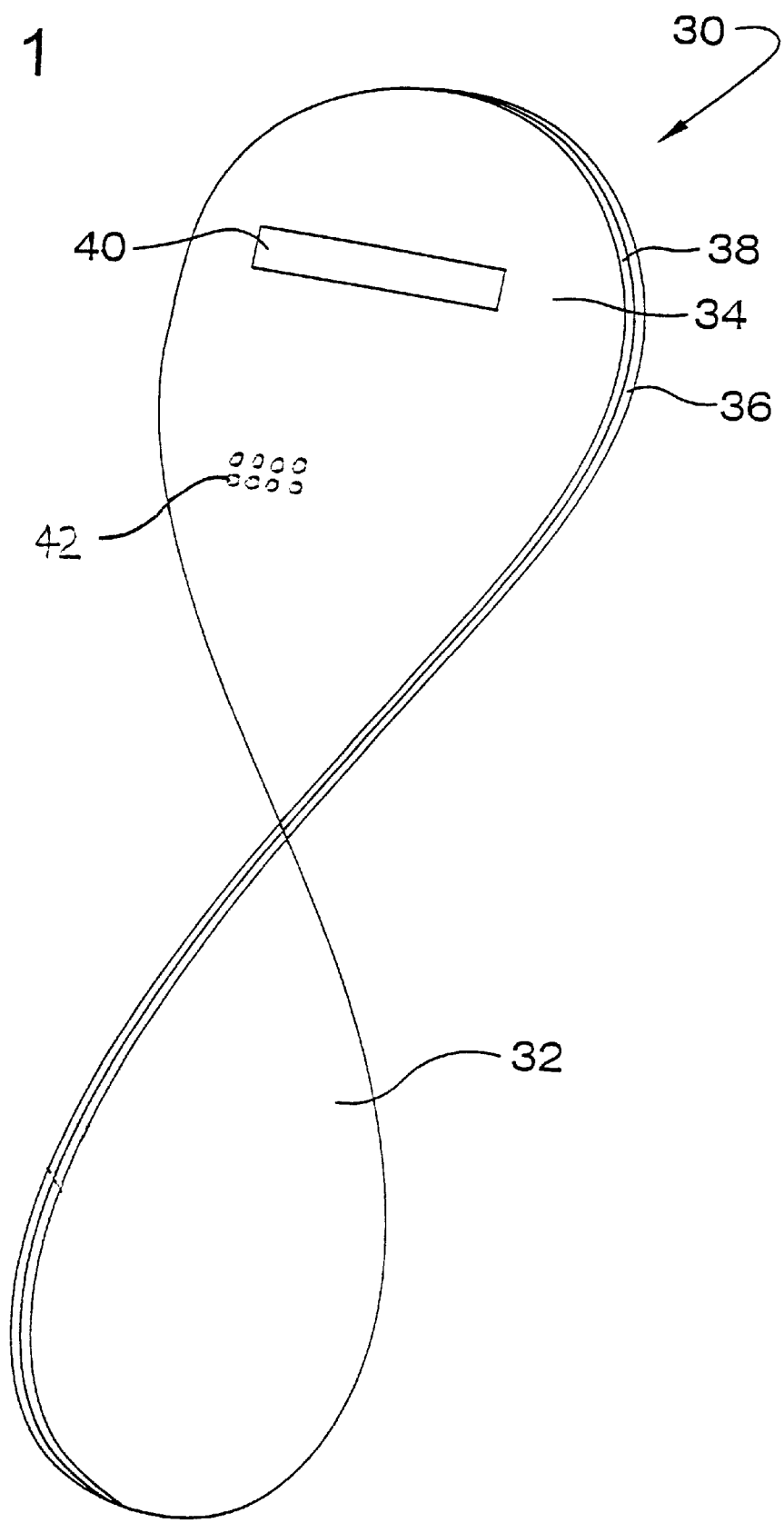
FIG. 1 is a perspective view of a pliable toilet training pad in accordance with the present invention.

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Disposable" refers to articles which are designed to be discarded after a limited use rather than being laundered or otherwise restored for reuse.

(c) "Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

(d) "Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "non-wettable" or hydrophobic.

(e) "Integrated" is used to refer to various portions of a single unitary element rather than separate structures bonded to or placed with or placed near one another.

(f) "Layer" when used in the singular can have the dual meaning of a single element or a plurality of elements.

(g) "Liquid impermeable," when used in describing a layer or multi-layer laminate means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

(h) "Liquid permeable" refers to a material present in one or more layers, such as a film, nonwoven fabric, or open-celled foam, which is porous, and which is water permeable due to the flow of water and other aqueous liquids, such as urine, through the pores. The pores in the film or foam, or spaces between fibers or filaments in a nonwoven web, are large enough and frequent enough to permit leakage and flow of liquid water through the material.

(i) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

(j) "Nonwoven" and "nonwoven web" refer to materials and webs of material which are formed without the aid of a textile weaving or knitting process.

(k) "Pliable" refers to materials which are compliant and which will readily conform to the general shape and contours of the wearer's body.

(l) "Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and atactic symmetries.

(m) "Spunbond" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

(n) "Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

(o) "Surface" includes any layer, film, woven, nonwoven, laminate, composite, or the like, whether pervious or impervious to air, gas, and/or liquids.

(p) "Surge Layer" refers to a layer typically comprised of nonwoven materials that can absorb a large stream or gush of liquid and release it slowly into another layer or layers.

(q) "Thermoplastic" describes a material that softens when exposed to heat and which substantially returns to a nonsoftened condition when cooled to room temperature.

(r) "Three dimensional" refers to a garment similar to underwear, shorts or pants in that it has continuous leg and waist openings that are bounded by material of which the garment is made. The garment may or may not have manually tearable seams.

DETAILED DESCRIPTION OF THE PREFERRED EMBODIMENTS

In accordance with the present invention, it has been discovered that an effervescent agent can be strategically positioned in a child's toilet training pant or other undergarment such that upon urination the effervescent agent releases gas to alert the wearer that urination has occurred. The wearer may be alerted of the urination either through feeling the release of the gas on the skin, or by feeling a mild concussive (i.e., "popping," "crackling," "bubbling" or "fizzing") sensation on the skin, or a combination thereof. The toilet training article in accordance with the present invention can be used in conjunction with an disposable or non-disposable absorbent undergarment to alert the wearer that urination has occurred while reducing potential adverse effects of prolonged contact between the skin and voided urine. Although discussed primarily in the context of toilet training of children, it should be understood that the present invention and its function are also applicable as an adult personal care product such as in absorbent incontinence undergarments and the like.

Referring to FIG. 1, there is shown a pliable toilet training pad 30 in accordance with the present invention. The toilet training pad comprises a pliable substrate having a body side 32 and an outer side 34. The body side faces the skin of the wearer during wear, generally in the crotch and/or buttocks region, while the outer side faces away from the skin of the wearer. As illustrated in FIG. 1, the toilet training pad is of layered construction and comprises a liner layer 36 and an absorbent core layer 38. Although illustrated in FIG. 1 with layered construction having two distinct, separate layers, and discussed herein primarily as having a liner and an absorbent core layer, it should be recognized that the toilet training pad of the present invention could be comprised of a single layer substrate comprised of, for example, a liner, or may be comprised of numerous different layers which may vary in absorbent capacity, thickness, material of construction, intended purpose, etc. Again referring to FIG. 1, outer side 34 may optionally contain attachment means 40 for releasably attaching the toilet training pad to an undergarment, such as a disposable undergarment. An effervescent agent 42 is typically disposed on at least a part of the outside face 34 of the toilet training pad such that upon urination, the effervescent agent releases gas in close proximity to the skin of the wearer to alert the wearer that urination has occurred. Alternatively, or in addition, the effervescent agent may be located on at least part of the inside face or on or between one or more other layers of the pad as described below.

The effervescent agent-containing toilet training pad of the present invention may be a single layer or may be of layered construction and may be comprised of a plurality of fibers which may be woven, nonwoven, or a combination thereof. The fibers may be bi-component, hollow, natural or synthetic, or a combination thereof, and may be hydrophilic or hydrophobic in nature, and may be, for example, a short staple fiber or a longer more continuous fiber generally found in meltblown and spunbond webs. Other suitable webs include bonded carded webs, air laid webs, wet laid webs, solution spun webs, porous films and generally any porous webs which have sufficient strength to be used as a liner for personal care absorbent products. Polyolefins, polyesters, cellulosics, polyacetates, and polyacrylate thermoplastics are some examples of polymers from which the fibers can be formed. One or more layers of the toilet training pad of the present invention may be liquid permeable and comprised of, for example, a liquid permeable film, tissue, fabric, or the like. One or more layers may also be liquid impermeable and comprised of, for example, a web or sheet of plastic film such as polyethylene, polypropylene, polyvinyl chloride, or similar material, or a nonwoven, fibrous web which has been suitably constructed and arranged to be substantially liquid impermeable. The toilet training pad of the present invention may also contain one or more superabsorbent and/or surge layers, or other layers which may be used alone or in combination with one or more layers described above.

As used herein, an effervescent agent means a material or compound that is capable of rapidly releasing gas upon contact with urine to cause a mild concussive or "popping" or "crackling" sensation on a wearer's skin or a mixture of compounds that, when contacted or mixed together and wetted with urine, produces a gaseous product and a "bubbling" or "fizzing" feeling on the wearer's skin. Thus, the effervescent agent may be a solid material (e.g., a crystal matrix) in which a pressurized gas is trapped and that gas is released upon contact with voided urine. Alternatively, the effervescent may be a mixture of compounds which when contacted or mixed together and wetted with urine, react and produce a non-toxic, gaseous reaction product without releasing a substantial amount of heat. The effervescent agents used in accordance with the present invention are substantially non-hazardous when contacted with human skin.

In one embodiment of the present invention, the effervescent agent may be a urine soluble solid material produced in such a manner such that a pressurized gas is trapped within cells located in the solid material. When the solid material having pressurized gas containing cells is contacted with urine, it begins to dissolve and the pressurized gas is released from the cells creating a noticeable sensation on the wearer's skin which may be felt as a rush of gas over the skin or as a "popping," "crackling" "bubbling" or "fizzing" sensation due to the release of the gas. This sensation, whether by a rush of gas or by a "popping," "crackling," "bubbling" or "fizzing" sensation alerts the wearer to the urination. In this embodiment, the effervescent agent may comprise a sugar compound such as a mono-saccharide, di-saccharide, or poly-saccharide which has been infused with a gas that is substantially non-reactive with human skin such as carbon dioxide, air, nitrogen, argon, helium, etc. Specific examples of saccharides that can be used in accordance with the present invention to create an effervescent agent include glucose, fructose, sucrose, lactose, maltose, dextrin, cyclodextrin, and the like, alone or in combination. Also, a mixture of sucrose with corn syrup (containing glucose, maltose, and dextrin) can be used in accordance with this embodiment of the present invention to provide an gas-containing effervescent agent. Other examples of compounds which are capable of being prepared in such as manner as to trap pressurized gas in cells include, for example, water soluble compounds such as salts and alkali halides and alkaline earth metal halides. Specific salts useful in the present invention include, for example, sodium chloride, potassium chloride, potassium bromide, lithium chloride, cesium chloride, and the like. Typically, the cells have a diameter from about 5 micrometers to about 100 micrometers.

The non-reactive gas can be infused into the cells of the urine-soluble solid material to produce an effervescent agent useful in the present invention by first heating the starting material such as a sugar in a small amount of water until the material is dissolved. After dissolution of the material, the water is evaporated off leaving the material in a molten state. The molten material is then gasified by introducing an inert gas, such as carbon dioxide, at a superatmospheric pressure into a closed vessel containing the molten material. The melt is agitated during gasification to ensure intimate contact between the molten material and the gas. Pressures of, for example, between about 50 psig (340 kPa) and about 1000 psig (6890 kPa) may be utilized to infuse the gas into the material. After gas infusion, the molten material is allowed to solidify while maintained in the closed vessel to produce an effervescent agent in accordance with the present invention. This procedure of producing a gas containing solid material is fully set forth in U.S. Pat. No. 4,289,794, which is hereby incorporated by reference. The above procedure can produce effervescent agents containing cells of pressurized gas from about 50 psig (340 kPa) to about 900 psig (6200 kPa) which, when exposed to urine, allow the release of the trapped gas causing a mild concussive effect or a "popping" or "crackling" next to the skin to alert the wearer that urination has occurred. Typically, from about 0.1 grams to about 15 grams of gas-containing effervescent agent are incorporated into the toilet training pad of the present invention to alert the wearer that urination has occurred.

In another embodiment of the present invention, an effervescent agent for use in or on a toilet training pad can be comprised of a mixture of compounds, such as an acid and a base, that when wetted with urine, react and produce a gaseous product and the wearer is alerted to having urinated through a "bubbling" or "fizzing" sensation on the skin. The effervescent agent could be in the form of a mixture of acid powders and base powders, liquid acids and liquid bases, or combinations thereof. The solid acids and bases can be introduced neat or in microencapsulated form into or onto the toilet training pad. Typically, if a liquid acid or base is utilized, it will be in microencapsulated form. One skilled in the art will recognize that the acids and bases utilized should be substantially non-reactive with each other until wetted with urine.

In a particular embodiment, the acid and base are separately encapsulated into microencapsulated shells. A combination of encapsulated shells containing acid and encapsulated shells containing base are then introduced into or onto the toilet training pad of the present invention. It will be recognized by one skilled in the art that with some acid/base combinations it may be possible to first mix the acid and base together and then introduce the mixture into an encapsulated shell which can be introduced into a pad in accordance with the present invention. In a separate embodiment, the acid and base are dispersed neat into or onto the toilet training pad of the present invention. It will also be recognized by one skilled in the art that a combination of encapsulated and neat acids and bases could be utilized. Any combination of compounds, such as an acid and a base, that is substantially non-reactive with each other until wetted with water or urine and that react to form at least one non-toxic gaseous product upon wetting may be utilized as an effervescent agent in accordance with the present invention. One skilled in the art will recognize that both acid strength and base strength may impact the amounts of acid and/or base utilized to form the effervescent agent. One skilled will also recognize that acid/base reactions are typically exothermic in nature and as such care should be taken to select appropriate acids and bases in consideration of the amount of heat produced by the reaction in close proximity to the skin of the wearer. Typically, the resulting acid/base mixture in the presence of the urine should have a resulting pH of from about 4.5 to about 7.5 to avoid skin damage. One skilled in the art will recognize that a buffering agent could be utilized in combination with the acid/base combination to help control the resulting pH of the acid/base mixture in the urine. One skilled in the art will also recognize that appropriate stoichiometric amounts of acids and bases would need to be utilized to obtain a mixture that when wetted with urine will produce a pH in the above range. One example of a suitable acid/base combination is shown in equation (1)

$$NaHCO_3 + KHC_4H_4O_6 \rightarrow KNaC_4H_4O_6 + H_2O + CO_2 \quad (1)$$

In equation (1), sodium bicarbonate and potassium bitartrate react in the presence of a liquid (urine) to form carbon dioxide gas and by-products. The production of the carbon dioxide gas alerts the wearer of the pad containing the acid and base that urination has occurred.

Another example of a suitable acid/base combination is shown in equation (2):

$$NaAl(SO_4)_2 + 3\, NaHCO_3 \rightarrow Al(OH)_3 + 2\, Na_2SO_4 + 3\, CO_2 \quad (2)$$

In equation (2), sodium aluminum sulfate and sodium bicarbonate react in the presence of liquid (urine) to form carbon dioxide gas and by-products. Other acids that can be used in combination with sodium bicarbonate to produce an effervescent agent in accordance with the present invention include ascorbic, lactic, glycolic, malic, tartaric, and fumaric. When mixed with sodium bicarbonate and contacted with urine, these acids produce carbon dioxide gas. This gas production can alert the wearer that urination has occurred.

The effervescent agents utilized in the present invention may be introduced directly into or onto a face of the toilet training pad as discussed below, or alternatively, first encapsulated into a shell material which releases the effervescent agent when wetted with urine. The microencapsulated shell is constructed of a material such that it will release the effervescent agent upon contact with urine and allow it to produce gas to alert the wearer that urination has occurred. The urine may cause the shell material to solubilize, disperse, swell, disintegrate, or may be urine permeable such that it disintegrates or discharges the effervescent agent upon contact with urine. Suitable shell materials include cellulose-based polymeric materials (e.g., ethyl cellulose), carbohydrate-based materials (e.g., starches and sugars) and materials derived therefrom (e.g., dextrins and cyclodextrins) as well as other materials compatible with human tissues. The microencapsulation shell thickness may vary depending upon the effervescent agent utilized, and is generally manufactured to allow the encapsulated effervescent agent to be covered by a thin layer of encapsulation material, which may be a monolayer or thicker laminate, or may be a composite layer. The microencapsulation layer should be thick enough to resist cracking or breaking of the shell during handling or shipping of the product or during wear which would result in breakage of the encapsulation material. The microencapsulation layer should also be constructed such that humidity from atmospheric conditions during storage, shipment, or wear will not cause a breakdown of the microencapsulation layer.

Effervescent agents, whether in neat or microencapsulated form, that are applied directly into or onto the toilet training pad can be located or be of a size such that the wearer is not cannot feel the encapsulated shell or solid against the skin prior to urination. Solid effervescent agents utilized neat may be introduced directly into the fabric of the liner, absorbent core, superabsorbent layer, or another layer and hence not have direct skin contact prior to urination. Neat effervescent agents and microencapsulated shells typically have a size from about 5 micrometers to about 40 micrometers, preferably from about 20 micrometers to about 35 micrometers.

The effervescent agents of the present invention, either in neat form, in microencapsulated form or a combination of both neat and microencapsulated form, are typically introduced into the toilet training pad of the present invention within or beneath the liner. The effervescent agent may be introduced beneath the liner and remain loose between the liner and a subsequent layer such as an absorbent core, surge layer, or other layer comprising the toilet training pad. Alternatively, if the toilet training pad of the present invention comprises solely a liner or a single layer, the effervescent agent is typically introduced into the material itself or onto the outer side of the liner which faces away from the wearer. In a particular embodiment, the effervescent agent may be introduced into or onto other layers of a toilet training pad such as a surge layer, a transfer layer, a tissue layer, a superabsorbent layer or another layer as the toilet training pad may be comprised of numerous layers.

In a particular embodiment, the effervescent agent of the present invention can be placed onto or into the toilet training pad and the pad positioned such that the effervescent agent is present in the crotch region of the wearer. Because the crotch region is the area of the body where the fluid is produced, the wearer will be alerted rapidly upon urination as the urine will rapidly induce the effervescent agent to release/produce a gas. Further, the crotch region contains a large number of nerve endings which can be stimulated by the release of gas by the effervescent agent upon urination. In another embodiment, the effervescent agent and toilet training pad can be located in the buttocks area. In another embodiment, the effervescent agent and pad may be located in both the crotch area and the buttocks area for maximum sensation.

Although the specific effervescent agent utilized may effect the overall sensation felt by the wearer upon urination, the amount of sensation from the gas released by the effervescent agent is typically a direct result of the amount of effervescent agent utilized. A sufficient amount of effervescent agent should be utilized such that the wearer can feel a concussive affect or a "bubbling," "popping," or "crackling" feeling due to the release of gas in the crotch, buttocks, or crotch and buttocks regions of the body.

Typically, the effervescent agents of the present invention are not simply introduced into or onto the toilet training pad of the present invention without a stabilizing mechanism to ensure the effervescent agents stay in the desired area. The effervescent agents of the present invention may be introduced into or onto the liner, absorbent core, or another layer of the toilet training pad of the present invention utilizing various methods including, for example, spray coating, slot coating and printing, or a combination thereof. With spray coating, the effervescent agents are first thoroughly mixed with a urine-soluble adhesive agent to disperse the effervescent agents throughout the adhesive material. It will be recognized that if an effervescent agent is comprised of separate compounds such as an acid and a base or a mixture of acids and a mixture of bases and the effervescent agent is to be utilized in neat form, care should be taken to ensure the adhesive is non-reactive with the acid and/or base or mixtures. Further, when and acid/base mixture is utilized as the effervescent agent, typically the acid is separately mixed with an adhesive and the base is separately mixed with an adhesive and the respective mixtures are applied in separate layers on the substrate.

The adhesive material can comprise a urine-soluble adhesive which will partially or completely dissolve upon urination by the wearer and allow the urine to contact the effervescent agent. Suitable urine-soluble adhesives include, for example, polyvinyl pyrrolidone and polyvinyl alcohol, and combinations thereof. After the urine-soluble adhesive and effervescent agent are thoroughly mixed, they can be applied onto the desired area of the toilet training pad of the present invention by spray coating, knifing, or roller coating, for example, and allowed to dry. The urine-soluble adhesive-effervescent agent mixture adheres to the liner, absorbent core, or another layer where it is retained until wetted with urine. Upon urination, the adhesive releases the effervescent agent such that may release or produce gas and alert or signal the wearer. Typically, the effervescent/adhesive mixture comprises from about 5% to about 50% effervescent agent by weight, preferably from about 10% to about 40% effervescent by weight. It will be recognized by one skilled in the art that the mixture ratio of the effervescent and adhesive may vary depending upon the material construction upon which the mixture is sprayed. In a particular embodiment, a first layer comprising an effervescent agent and an adhesive are sprayed onto the substrate. After the first layer has dried, a second layer comprising as adhesive agent is sprayed on top of the first layer. This combination of two layers may help ensure that the effervescent agent does not produce gas prior to urination.

Similar to spray coating, effervescent agents may be introduced into or onto the toilet training pad of the present invention through slot coating. In slot coating, an adhesive-effervescent mixture as discussed above is introduced directly onto the desired area of the pad in "slots" or discrete row patterns. Upon urination by the wearer, the adhesive allows a release of the effervescent agent such that it may produce a gas. Slot coating may be advantageous in certain applications where it is not desirable to coat the entire surface with an adhesive. In some circumstances, an adhesive coating over an entire surface may retard quick absorption of the urine into the absorbent core. When slot coating is utilized, channels are created where no adhesive is present and urine may drain quickly. Slot coating may also be advantageous in certain applications where precise control of the location of the effervescent agent is desired. Typically, the rows of effervescent/adhesive are spaced on the order of from about 0.1 inches to about 3 inches apart from each other, preferably from about 0.2 inches to about 2 inches apart from each other, and most preferably about 0.25 inches apart from each other. Generally, the rows are evenly spaced across the surface upon which they are applied, but may be spaced in specific patterns with varying spacing if desired. In a particular embodiment utilizing an effervescent agent comprised of an acid/base mixture, slot coating can be utilized to create alternating rows of acid/adhesive-base/adhesive to ensure that the acid and base do not react together prior to urination. As described above in regard to spray coating, a second layer of adhesive may be introduced on top of a first slot-coated layer comprising both an effervescent agent and an adhesive to further ensure that the effervescent agent does not release gas prior to urination.

The effervescent agents of the present invention can also be introduced onto or into a gas-permeable liner, absorbent core, or another layer of the training pad of the present invention through the use of a vacuum driving force. The effervescent agent is positioned on the liner, absorbent core, or another layer while a vacuum driving force is applied to the opposite side of the liner, core, or layer to drive the effervescent agent into the fabric matrix of the liner, core, or other layer. Varying degrees of vacuum can be applied depending upon the depth the effervescent agent is to be positioned within the substrate. In this embodiment, no urine-soluble adhesive is necessary. Once in the fabric matrix of the pad, the effervescent agent is retained until urination occurs at which time the urine contacts the effervescent agent. This embodiment is particularly useful for solid or powdered effervescent agents which are applied neat. Alternatively, electrostatic forces or other means may be utilized to stabilize the effervescent agent on the surface of the liner or core.

In an alternative embodiment of the present invention, the acid and/or base compounds which may be combined to produce an effervescent agent may be incorporated into a hydrophilic microsponge material which is subsequently used in combination with the pad of the present invention.

The microsponge performs the same function as the microencapsulation shell described above. The hydrophilic microsponge containing the effervescent agent is introduced onto or into the toilet training pad of the present invention as discussed above. Suitable materials comprising the hydrophilic microsponge include, for example, acrylate polymers and acrylate copolymers of a hydrophilic nature.

To incorporate either a solid or a liquid acid and/or base into the hydrophilic microsponge material, the acid or base can be introduced into an suitable volatile, such as an alcohol or water and dissolved. The solution containing the dissolved acid and/or base is contacted with and absorbed into the microsponge material. After absorption, the solvent is driven off by evaporation or other means known in the art, leaving a dry hydrophilic microsponge material containing the acid and/or base. Because of the structure of the sponge, the effervescent agent is suitably stable as it would need to travel a tortuous path to exit the sponge. The acid and/or base is located in the interstitial spaces in the sponge and, upon flooding of the sponge upon urination, is driven out of the interstitial spaces by the urine and react to produce a gaseous product. The acid and/or base-containing hydrophilic microsponges of the present invention may be introduced onto or into the toilet training pad of the present invention similar to the encapsulated effervescent agents discussed above.

Figure 2:
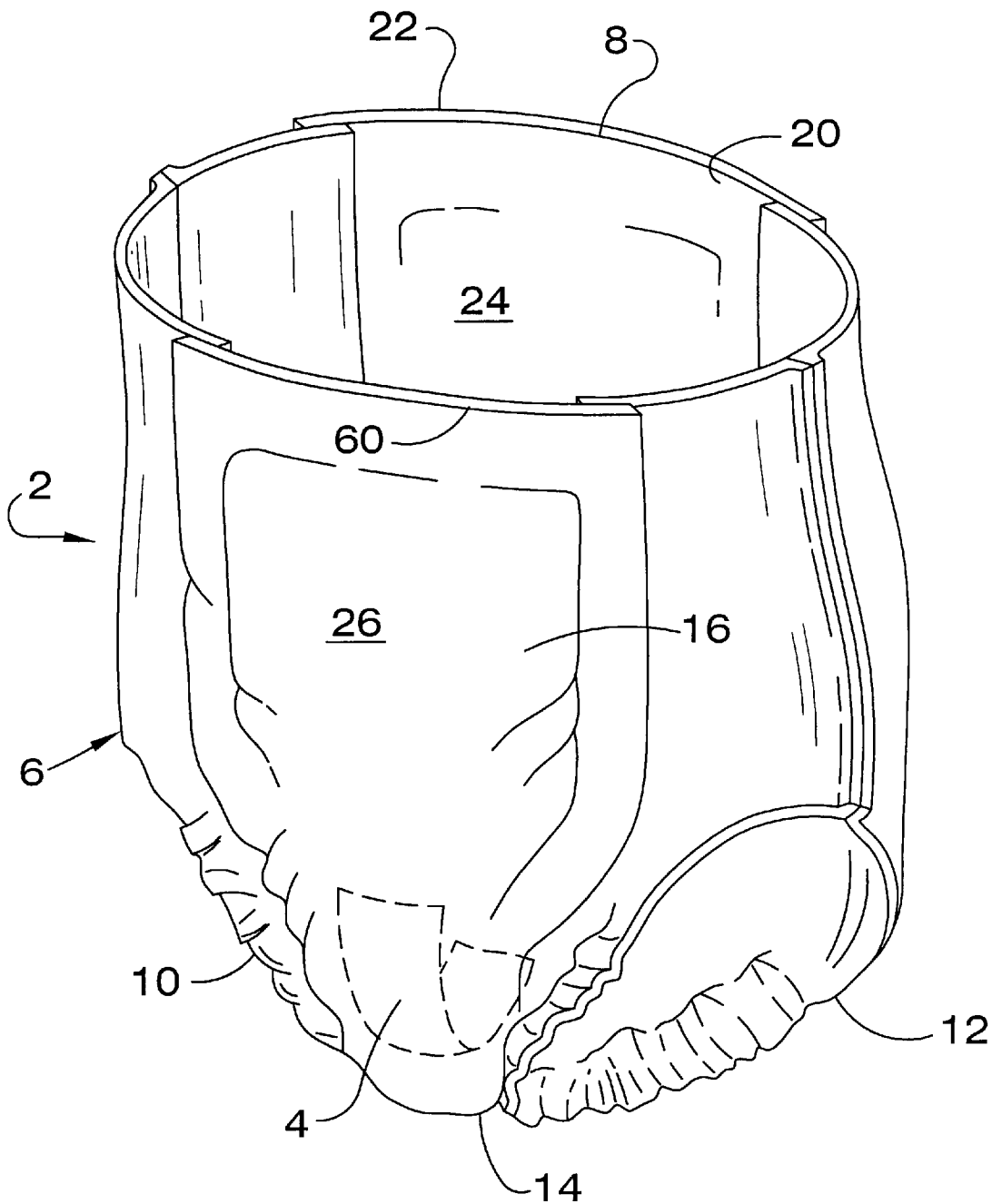
FIG. 2 is a perspective view of a disposable toilet training article in accordance with the present invention, which includes a pliable toilet training pad.

Referring now to FIG. 2, there is shown a toilet training article 2 for purposes of illustration of a toilet training pad 4 of the present invention which is attached to the inside of a three-dimensional, disposable, toilet training pant 6. At least a portion of the toilet training pad 4 contains an effervescent agent in accordance with the present invention to alert the wearer when urination has occurred by allowing the effervescent agent to release gas upon urination.

Although the toilet training pad in FIG. 2 is illustrated as part of toilet training pants, the training pad may also be used in conjunction with other garments, such as underwear, diapers, diaper pants, washable or reusable absorbent garments such as cloth training pants, cloth diapers, plastic training pants, or the like. The effervescent containing toilet training pad may either be part of the garment as a whole (i.e., integrated into the garment when manufactured) or may be in the form of an insert which may be permanently or releasably attached to any of the aforementioned garments by the manufacturer or the consumer. If the toilet training pad containing the effervescent agent is manufactured in the form of an insertable pad, it preferably has attachable means thereon to allow the consumer to easily attach the pad to an undergarment. Suitable attachable means may include, for example, adhesive strips, thermal bonds, ultrasonic bonds, hook and loop type fasteners. This allows the consumer the choice of the type of garment to use with the toilet training pad of the present invention. Also, the consumer can control when the toilet training pad is used.

Referring again to FIG. 2, the training pant 6 is a three-dimensional garment and defines a waist opening 8 and two leg openings 10 and 12. A crotch region 14 is generally located between the leg openings 10 and 12 and comprises that portion of the training pant which, when worn, is positioned between the legs of the wearer and covers the lower torso of the wearer. The crotch region is typically where the toilet training pad containing the effervescent agent is located. A front waist region 16 of the training pants 6 generally extends from the crotch region 14 to a front end 60 of the pants, and a back waist region 20 extends from the crotch region 14 to a back end 22 of the pants. The training pant 6 also includes an inner surface 24 and an opposite outer surface 26. By way of illustration only, various materials and methods for constructing training pants are disclosed in PCT Pat. No. Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference. When the training pant is worn, the toilet training pad is positioned near or against the skin of the wearer and located so that urine contacts the toilet training pad during urination. The toilet training pad or toilet training pad area, which may encompass both the crotch region and the buttocks region, contains the effervescent agent in accordance with the present invention.

In view of the above, it will be seen that the several embodiments of the invention are achieved. As various changes could be made in the above-described toilet training pad without departing from the scope of the invention, it is intended that all matter contained in the above description be interpreted as illustrative and not in a limiting sense.

What is claimed is:

1. An article for use in conjunction with an undergarment in the form of a pad comprising a pliable substrate and an effervescent agent encapsulated in a shell material, the shell material being capable of releasing the effervescent agent when wetted with urine, the substrate having a body side face and an outside face, the body side face facing the skin of the wearer when the article is worn, the effervescent agent comprising a matrix structure comprising a sugar compound and having cells distributed therein which contain a gas under pressure, the effervescent agent being disposed on the substrate in a manner such that when the pad is wetted with urine, the gas is released from the effervescent agent to alert the wearer of urination.

2. An article as set forth in claim 1 wherein the sugar compound is selected from the group consisting of monosaccharides, di-saccharides, and polysaccharides.

3. An article as set forth in claim 1 wherein the sugar compound is selected from the group consisting of glucose, fructose, lactose, maltose, sucrose, dextrins, and cyclodextrins.

4. An article as set forth in claim 1 wherein the gas under pressure is selected from the group consisting of carbon dioxide, nitrogen, argon, air, and helium.

5. An article as set forth in claim 1 wherein the average diameter of the cells is from about 5 micrometers to about 100 micrometers.

6. An article as set forth in claim 1 wherein pressure of the gas in the cells is from about 50 psig to about 900 psig.

7. An article as set forth in claim 1 wherein from about 0.1 grams to about 15 grams of effervescent agent is disposed on the substrate.

8. An article as set forth in claim 1 wherein the shell material comprises a material selected from the group consisting of ethyl cellulose, starches, sugars, dextrins, and cyclodextrins.

9. An article as set forth in claim 1 wherein the shell material is urine-dispersable.

10. An article as set forth in claim 1 wherein the shell material is urine-swellable.

11. An article as set forth in claim 1 wherein the shell material is urine-permeable.

12. An article as set forth in claim 1 wherein the shell material disintegrates when wetted with urine.

13. An article as set forth in claim 1 wherein the effervescent agent is disposed on the outside face of the substrate.

14. An article as set forth in claim 1 wherein the substrate is of layered construction and comprises a liner and absorbent core layer, the liner facing the skin of the wearer when the article is worn, and the effervescent agent being disposed beneath the liner.

15. An article as set forth in claim 14 wherein the effervescent agent is disposed on the absorbent core.

16. An article as set forth in claim 14 wherein the substrate further comprises a superabsorbent layer and the effervescent agent is disposed within the superabsorbent layer.

17. An article for use in conjunction with an undergarment in the form of a pad comprising a pliable substrate and an effervescent agent encapsulated in a shell material, the shell material being capable of releasing the effervescent agent when wetted with urine, the substrate having a body side face and an outside face, the body side face facing the skin of the wearer when the article is worn, the effervescent agent comprising a matrix structure comprising a salt compound and having cells distributed therein which contain a gas under pressure, the effervescent agent being disposed on the substrate in a manner such that when the pad is wetted with urine, the gas is released from the effervescent agent to alert the wearer of urination.

18. An article as set forth in claim 17 wherein the salt compound is selected from the group consisting of sodium chloride, potassium chloride, potassium bromide, lithium chloride, and cesium chloride.

19. An article as set forth in claim 17 wherein the gas under pressure is selected from the group consisting of carbon dioxide, nitrogen, argon, air, and helium.

20. An article as set forth in claim 17 wherein from about 0.1 grams to about 15 grams of effervescent agent is disposed on the substrate.

21. An article as set forth in claim 17 wherein the shell material comprises a material selected from the group consisting of ethyl cellulose, starches, sugars, dextrins, and cyclodextrins.

22. An article as set forth in claim 17 wherein the shell material is urine-dispersable.

23. An article as set forth in claim 17 wherein the shell material is urine-swellable.

24. An article as set forth in claim 17 wherein the shell material is urine-permeable.

25. An article as set forth in claim 17 wherein the shell material disintegrates when wetted with urine.

26. An article as set forth in claim 17 wherein the effervescent agent is disposed on the outside face of the substrate.

27. An article as set forth in claim 17 wherein the substrate is of layered construction and comprises a liner and absorbent core layer, the liner facing the skin of the wearer when the article is worn, and the effervescent agent being disposed beneath the liner.

28. An article as set forth in claim 26 wherein the effervescent agent is disposed on the absorbent core.

29. An article as set forth in claim 26 wherein the substrate further comprises a superabsorbent layer and the effervescent agent is disposed within the superabsorbent layer.

30. An article for use in conjunction with an undergarment in the form of a pad comprising a pliable substrate and an effervescent agent encapsulated in a shell material, the shell material being capable of releasing the effervescent agent when wetted with urine, the substrate having a body side face and an outside face, the body side face facing the skin of the wearer when the article is worn, the effervescent agent having a size of from about 5 micrometers to about 40 micrometers and comprising a matrix structure comprising a sugar compound and having cells distributed therein which contain a gas under pressure, and the effervescent agent being disposed on the substrate in a manner such that when the pad is wetted with urine, the gas is released from the effervescent agent to alert the wearer of urination.

31. An article as set forth in claim 30 wherein the effervescent agent has a size of from about 20 to about 35 micrometers.

32. An article as set forth in claim 30 wherein the gas under pressure is selected from the group consisting of carbon dioxide, nitrogen, argon, air, and helium.

33. An article as set forth in claim 30 wherein from about 0.1 grams to about 15 grams of effervescent agent is disposed on the substrate.

34. An article for use in conjunction with an undergarment in the form of a pad comprising a pliable substrate and an effervescent agent encapsulated in a shell material, the shell material being capable of releasing the effervescent agent when wetted with urine, the substrate having a body side face and an outside face, the body side face facing the skin of the wearer when the article is worn, the effervescent agent having a size of from about 5 micrometers to about 40 micrometers and comprising a matrix structure comprising a salt compound and having cells distributed therein which contain a gas under pressure, and the effervescent agent being disposed on the substrate in a manner such that when the pad is wetted with urine, the gas is released from the effervescent agent to alert the wearer of urination.

35. An article as set forth in claim 34 wherein the effervescent agent has a size of from about 20 to about 35 micrometers.

36. An article as set forth in claim 34 wherein the gas under pressure is selected from the group consisting of carbon dioxide, nitrogen, argon, air, and helium.

37. An article as set forth in claim 34 wherein from about 0.1 grams to about 15 grams of effervescent agent is disposed on the substrate.

\* \* \* \* \*